United States Patent
Shen et al.

(10) Patent No.: US 10,704,017 B2
(45) Date of Patent: Jul. 7, 2020

(54) CELL CULTURE CARRIER MODULE AND CELL CULTURE SYSTEM

(71) Applicant: Industrial Technology Research Institute, Hsinchu (TW)

(72) Inventors: Ying-Wen Shen, Miaoli County (TW); Ing-Kae Wang, Hsinchu (TW); Chia-Jung Lu, Taichung (TW); Yea-Tzy Deng, Hsinchu (TW); Yu-Bing Liou, Hsinchu (TW); Sing-Ying Hsieh, Hsinchu (TW); Hsin-Hsin Shen, Hsinchu County (TW); Hsiu-Ying Wang, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 246 days.

(21) Appl. No.: 15/854,789

(22) Filed: Dec. 27, 2017

(65) Prior Publication Data

US 2018/0223238 A1    Aug. 9, 2018

Related U.S. Application Data

(60) Provisional application No. 62/454,067, filed on Feb. 3, 2017.

(30) Foreign Application Priority Data

Nov. 10, 2017 (TW) .............................. 106138863 A

(51) Int. Cl.
C12M 1/24 (2006.01)
C12M 1/42 (2006.01)
(Continued)

(52) U.S. Cl.
CPC .............. *C12M 23/52* (2013.01); *C12M 3/04* (2013.01); *C12M 23/08* (2013.01); *C12M 23/26* (2013.01);
(Continued)

(58) Field of Classification Search
CPC ...... C12M 23/52; C12M 23/46; C12M 23/08; C12M 23/40; C12M 23/02; C12M 25/00;
(Continued)

(56) References Cited

U.S. PATENT DOCUMENTS

| 5,266,476 A | 11/1993 | Sussman et al. |
| 5,707,859 A | 1/1998 | Miller et al. |

(Continued)

FOREIGN PATENT DOCUMENTS

| CN | 1435482 | 8/2003 |
| CN | 1895687 | 1/2007 |

(Continued)

OTHER PUBLICATIONS

Machine Translation of JP2005-262206 A. (Year: 2019).*
(Continued)

*Primary Examiner* — Michael L Hobbs
(74) *Attorney, Agent, or Firm* — JCIPRNET

(57) ABSTRACT

A cell culture carrier module and a cell culture system having the same are provided. A cell tank and a culture medium module respectively communicate with the carrier module. The carrier module includes a reactor, a first fixer, a second fixer and a plurality of cell culture carriers. The reactor has a chamber and at least one inlet/outlet. The inlet/outlet communicates with the chamber. The first fixer is fixed to the reactor and located in the chamber. The second fixer is disposed in the chamber and is movable relative to the first fixer. Two ends of each cell culture carrier are fixed to the first fixer and the second fixer, respectively. The cell culture carriers are in an untwisted state or a twisted state according to a variation in a distance between the first fixer and the second fixer due to a movement of the second fixer.

19 Claims, 13 Drawing Sheets

(51) Int. Cl.
*C12M 1/00* (2006.01)
*C12M 3/04* (2006.01)
*C12M 1/12* (2006.01)
*C12M 3/00* (2006.01)
*C12M 1/34* (2006.01)

(52) U.S. Cl.
CPC ............ *C12M 23/40* (2013.01); *C12M 23/46* (2013.01); *C12M 25/00* (2013.01); *C12M 35/04* (2013.01); *C12M 35/06* (2013.01); *C12M 41/40* (2013.01)

(58) Field of Classification Search
CPC ...... C12M 25/14; C12M 35/04; C12M 35/06; C12M 41/40; C12M 41/00; C12M 3/04
See application file for complete search history.

(56) References Cited

U.S. PATENT DOCUMENTS

| | | | |
|---|---|---|---|
| 6,214,618 B1 | 4/2001 | Hillegas et al. | |
| 6,875,605 B1 | 4/2005 | Ma | |
| 7,033,823 B2 | 4/2006 | Chang | |
| 8,080,418 B2 | 12/2011 | Noll et al. | |
| 8,623,398 B2 | 1/2014 | Altman et al. | |
| 2003/0093034 A1 | 5/2003 | Chang et al. | |
| 2003/0143727 A1* | 7/2003 | Chang | C12M 23/26 435/289.1 |
| 2008/0194010 A1 | 8/2008 | Liu | |
| 2008/0293133 A1 | 11/2008 | Reid et al. | |
| 2010/0124775 A1 | 5/2010 | Peeters et al. | |
| 2011/0238178 A1 | 9/2011 | Downes et al. | |
| 2012/0308531 A1 | 12/2012 | Pinxteren et al. | |
| 2013/0144400 A1 | 6/2013 | Day et al. | |
| 2014/0005797 A1 | 1/2014 | Park et al. | |
| 2014/0105951 A1 | 4/2014 | Altman et al. | |
| 2017/0073625 A1 | 3/2017 | Kasuto et al. | |
| 2017/0166859 A1* | 6/2017 | Wang | C12M 23/44 |

FOREIGN PATENT DOCUMENTS

| | | | | |
|---|---|---|---|---|
| CN | 101245313 | | 8/2008 | |
| CN | 101541946 | | 9/2009 | |
| CN | 102099462 | | 6/2011 | |
| CN | 102127505 | | 7/2011 | |
| CN | 102666851 | | 9/2012 | |
| CN | 103100119 | | 5/2013 | |
| CN | 103409361 | | 11/2013 | |
| CN | 104342370 | | 2/2015 | |
| EP | 2177603 | | 4/2010 | |
| JP | 2005-653496 A | * | 9/2005 | ............ B01D 63/02 |
| TW | 200624558 | | 7/2006 | |
| TW | I259203 | | 8/2006 | |
| TW | I270576 | | 1/2007 | |
| TW | 200835790 | | 9/2008 | |
| TW | 200942615 | | 10/2009 | |
| TW | M381634 | | 6/2010 | |
| TW | 201231153 | | 8/2012 | |
| TW | I374185 | | 10/2012 | |
| TW | 201335368 | | 9/2013 | |
| TW | 201643242 | | 12/2016 | |
| WO | 2005010172 | | 2/2005 | |
| WO | 2015054677 | | 4/2015 | |

OTHER PUBLICATIONS

Teng Ma, et al., "Development of an in Vitro Human Placenta Model by the Cultivation of Human Trophoblasts in as Fiber-Based Bioreactor System," Tissue Engineering, vol. 5, No. 2, Apr. 1999, pp. 91-102.

"Office Action of Taiwan Counterpart Application", dated Jan. 10, 2017, p.1-p.8, in which the listed references were cited.

"Office Action of Taiwan Counterpart Application", dated Nov. 29, 2018, p. 1-p. 10.

"Office Action of China Related Application, application No. 201511022561.2", dated Dec. 2, 2019, p. 1-p. 7.

* cited by examiner

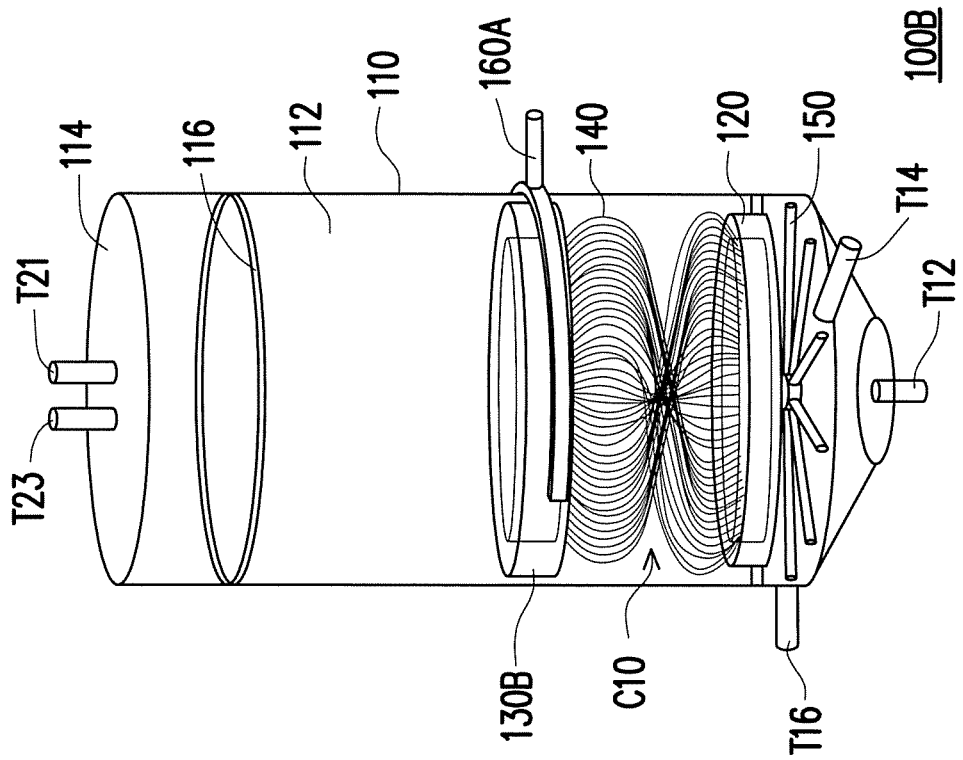
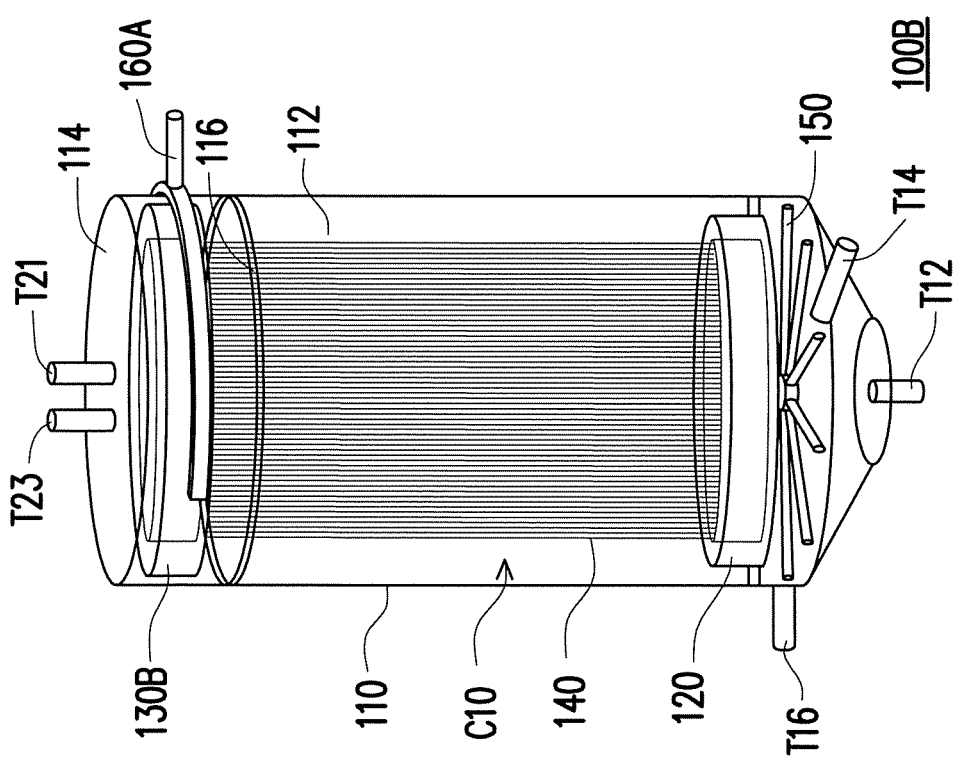
FIG. 2A
FIG. 2B

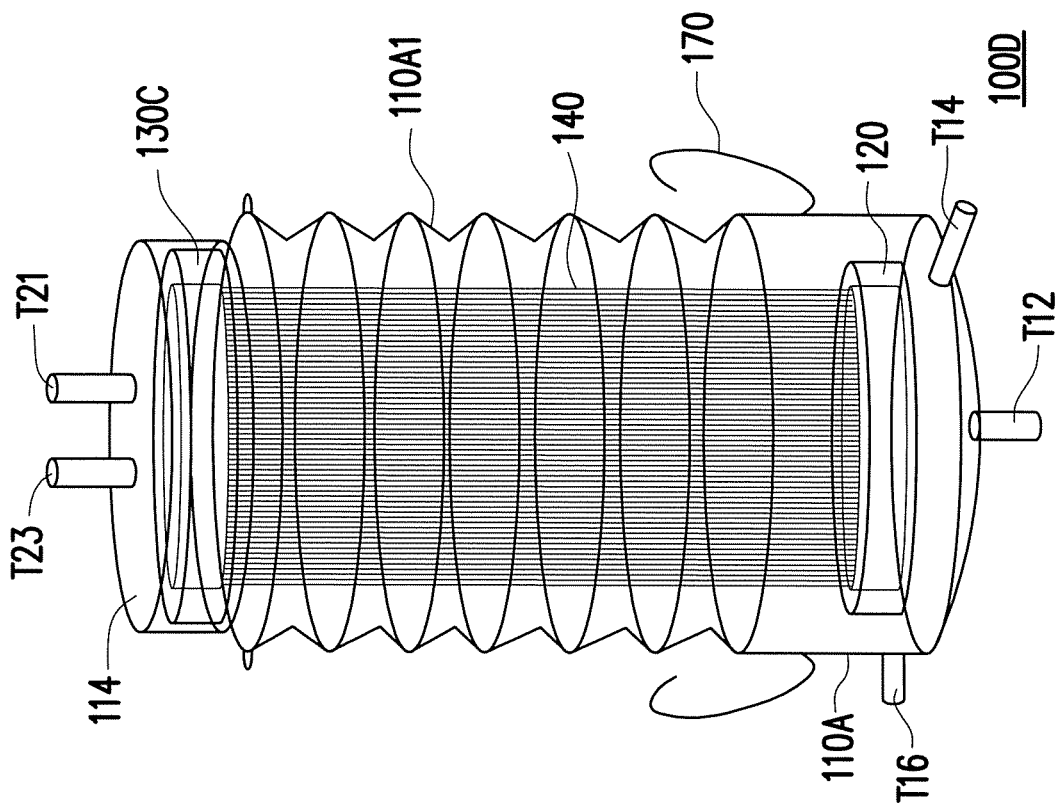
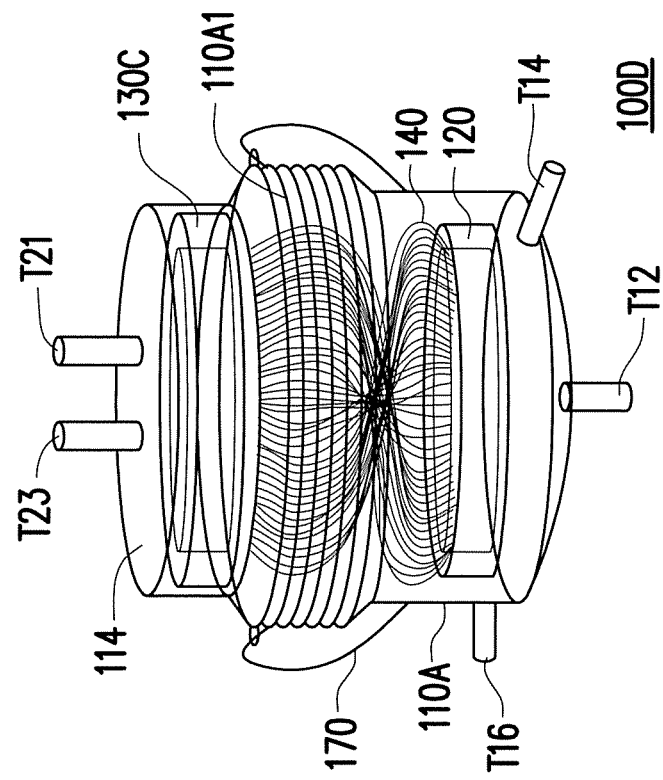
FIG. 4A
FIG. 4B

CELL CULTURE CARRIER MODULE AND CELL CULTURE SYSTEM

CROSS-REFERENCE TO RELATED APPLICATION

This application claims the priority benefit of U.S. provisional application Ser. No. 62/454,067, filed on Feb. 3, 2017 and Taiwan application serial no. 106138863, filed on Nov. 10, 2017. The entirety of each of the above-mentioned patent applications is hereby incorporated by reference herein and made a part of this specification.

TECHNICAL FIELD

The technical field relates to a cell culture carrier module and a cell culture system.

BACKGROUND

Current carrier scaffolds for cell mass production may be divided into two categories, one being natural materials such as collagen, chitosan, gelatin or the like, and the other being synthetic materials such as polycaprolactone (PCL), polystyrene (PS), polypropylene (PP), poly(lactic-co-glycolic acid) (PLGA) or the like. The natural materials are mostly materials derived from animal sources. Although the materials derived from animal sources have lower cytotoxicity and higher biocompatibility, they may carry undetectable animal contaminants. Therefore, the current trend is toward reducing or even eliminating the use of the materials derived from animal sources to reduce the risk of contamination.

In addition, among current commercially available cell carriers, all the synthetic materials except for alginate-based related products are difficult to degrade, thus causing challenges in recovering the cells. Since the alginate-based related products require a high concentration of calcium ions during cell culture, the cells may be damaged or a tendency to differentiation may be induced in some certain cells (e.g., mesenchymal stem cells). In addition, during degradation of alginate, it is necessary to use a calcium ion chelator, and improper usage thereof is very likely to cause damage to the cells. In addition, there is still room for improvement in key techniques for cell collection carrier scaffolds. Thus, current cell mass production technology still remains at a conventional two-dimensional flat plate culture method, and the process cannot be adapted to larger scale production.

Therefore, to find a carrier material suitable for rapid and mass growth of cells and yet devoid of animal contaminants and to enhance cell recovery rate and cell quality are both issues that researchers are eager to solve.

SUMMARY

According to one or more exemplary embodiments, a cell culture carrier module includes a reactor, a first fixer, a second fixer and a plurality of cell culture carriers. The reactor has a chamber and at least one inlet/outlet. The inlet/outlet communicates with the chamber. The first fixer is fixed to the reactor and located in the chamber. The second fixer is disposed in the chamber and is movable relative to the first fixer. Two ends of each of the cell culture carriers are fixed to the first fixer and the second fixer, respectively. The cell culture carriers are in an untwisted state or a twisted state according to a variation in a distance between the first fixer and the second fixer due to a movement of the second fixer.

According to one or more exemplary embodiments, a cell culture system includes a cell tank, a culture medium module and a carrier module. The cell tank and the culture medium module respectively communicate with the carrier module. The carrier module includes a reactor, a first fixer, a second fixer and a plurality of cell culture carriers. The reactor has a chamber and at least one inlet/outlet. The inlet/outlet communicates with the chamber. The first fixer is fixed to the reactor and located in the chamber. The second fixer is disposed in the chamber and is movable relative to the first fixer. Two ends of each of the cell culture carriers are fixed to the first fixer and the second fixer, respectively. The cell culture carriers are in an untwisted state or a twisted state according to a variation in a distance between the first fixer and the second fixer due to a movement of the second fixer.

Based on the above, in the cell culture carrier module and the cell culture system according to one or more exemplary embodiments, by the second fixer, the cell culture carrier can be controlled to switch between the untwisted state and the twisted state, and cell recovery rate and cell quality can thus be enhanced.

Several exemplary embodiments accompanied with figures are described in detail below to further describe the disclosure in details.

BRIEF DESCRIPTION OF THE DRAWINGS

FIG. 2A and FIG. 2B are schematic views of a cell culture carrier of a cell culture carrier module, in an untwisted state and a twisted state, respectively, according to another exemplary embodiment.

FIG. 4A and FIG. 4B are schematic views of a cell culture carrier of a cell culture carrier module, in a twisted state and an untwisted state, respectively, according to yet still another exemplary embodiment.

DETAILED DESCRIPTION OF DISCLOSED EMBODIMENTS

According to one or more exemplary embodiments, a cell culture carrier module and a cell culture system are provided capable of solving the problems concerning cell recovery rate and cell quality.

Figure 1B:
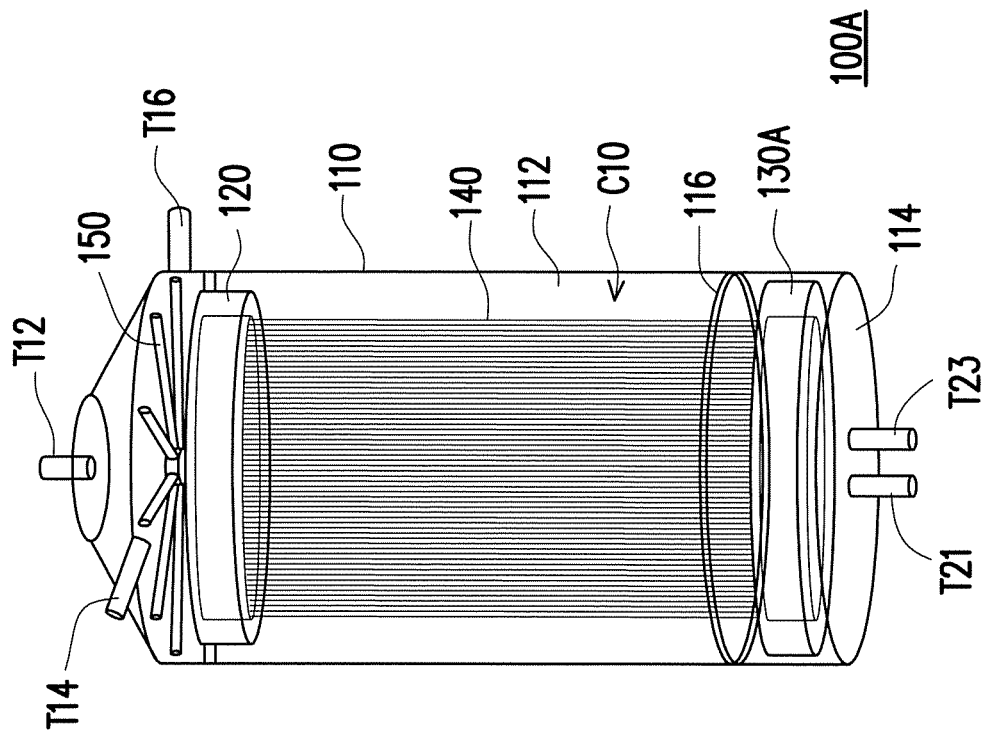
FIG. 1A and FIG. 1B are schematic views of a cell culture carrier of a cell culture carrier module, in a twisted state and an untwisted state, respectively, according to an exemplary embodiment.
Figure 1A:
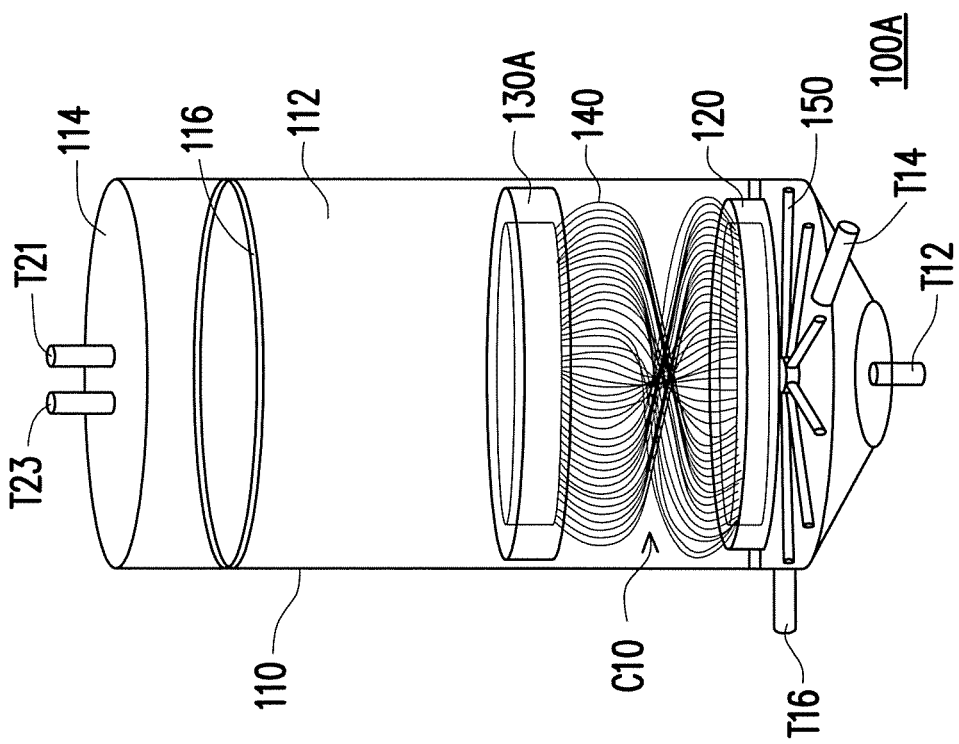

FIG. 1A and FIG. 1B are schematic views of a cell culture carrier of a cell culture carrier module, in a twisted state and an untwisted state, respectively, according to an exemplary embodiment. Referring to FIG. 1A and FIG. 1B, a cell culture carrier module 100A of the present embodiment includes a reactor 110, a first fixer 120, a second fixer 130A and a plurality of cell culture carriers 140. The reactor 110 has a chamber C10 and at least one inlet/outlet T12. The chamber C10 is configured to provide space for culturing cells. The inlet/outlet T12 communicates with the chamber C10. The first fixer 120 is fixed to the reactor 110 and located in the chamber C10. The second fixer 130A is disposed in the chamber C10 and is movable relative to the first fixer 120. Two ends of each of the cell culture carriers 140 are fixed to the first fixer 120 and the second fixer 130A, respectively. According to a variation in a distance between the first fixer 120 and the second fixer 130A due to a movement of the second fixer 130A, the cell culture carriers 140 may be in a twisted state as shown in FIG. 1A or an untwisted state as shown in FIG. 1B.

In other words, when the distance between the first fixer 120 and the second fixer 130A becomes less than a stretch length of the cell culture carriers 140 due to the movement of the second fixer 130A, the cell culture carriers 140 are rendered in the twisted state, as shown in FIG. 1A. The cell culture carriers 140 may have a strip shape. Thus, the strip-shaped cell culture carriers 140 may be used in limited space to obtain more area for cells to adhere to so as to increase the number of culturable cells, and it also becomes easier to maintain uniform distribution of nutrients in a cell culture medium, thereby ensuring quality of the cultured cells.

In addition, when the distance between the first fixer 120 and the second fixer 130A becomes roughly equal to the stretch length of the cell culture carriers 140 due to the movement of the second fixer 130A, the cell culture carriers 140 are rendered in the untwisted state, as shown in FIG. 1B. The cells may be detached from the cell culture carriers 140 during a change of state of the cell culture carriers 140 from the twisted state to the untwisted state. In addition, since the distance between the cell culture carriers 140 is increased, a substance (e.g., enzyme) for facilitating detachment of the cells from the cell culture carriers 140 may be injected, and the substance may easily reach all the cells to sufficiently perform a reaction, which conduces to enhancement of a cell recovery rate.

In the present embodiment, since the second fixer 130A is movably disposed in the chamber C10, when the reactor 110 is placed in the state as shown in FIG. 1A, the second fixer 130A moves downward to a position close to the first fixer 120 due to its own gravity. To change the cell culture carriers 140 to the untwisted state, the reactor 110 may be placed upside down as shown in FIG. 1B and changed to a state opposite the state in FIG. 1A. In this way, the second fixer 130A moves downward to a position away from the first fixer 120 due to its own gravity, and the cell culture carriers 140 are stretched by the first fixer 120 and the second fixer 130A and changed to the untwisted state. In addition, to improve mobility of the second fixer 130A, a weight block may be installed onto the second fixer 130A to ensure that the second fixer 130A can move by its own gravity.

From another point of view, when the cell culture carriers 140 are in the untwisted state, each of the cell culture carriers 140 is equivalent to a two-dimensional structure. When the cell culture carriers 140 are in the twisted state, each of the cell culture carriers 140 is equivalent to a three-dimensional structure. In FIG. 1A, each of the cell culture carriers 140 in the twisted state has a regular spiral shape. However, the cell culture carrier 140 may also be randomly twisted, and thus a plurality of cell culture carriers 140 in the twisted state may have a coiling shape. However, the disclosure is not limited thereto. In FIG. 1B, each of the cell culture carriers 140 in the untwisted state has a straight strip shape, and thus a plurality of cell culture carriers 140 in the untwisted state may be arranged in an array of parallel lines. However, the cell culture carriers 140 in the untwisted state may not be parallel to one another, or some of the cell culture carriers 140 may be slightly bent. However, the disclosure is not limited thereto.

A material of the cell culture carriers 140 includes, for example, polyester (PET), nylon, polyethylene (PE), polypropylene (PP), polyvinyl chloride (PVC), polystyrene (PS), polycarbonate (PC), ethylene vinyl acetate (EVA), polyurethane (PU) or the like. However, the disclosure is not limited thereto, and any material having fiber drawing properties may be used as the material for the cell culture carrier of the disclosure. In addition, each of the cell culture carriers 140 may be in the shape of a striped sheet, a threadlike sheet, or in any other suitable shape.

The cell culture carriers 140 may be a material to which cells can adhere or a material having cell adhesion properties after processing. The above processing methods include surface modification, surface coating, surface microstructurization or the like. Surface modification is achieved by, for example, performing plasma modification on a surface of the material to which cells can adhere, or a surface of a material to which cells cannot adhere to impart the cell adhesion properties to the surface, thereby facilitating adhesion of the cells. Surface coating includes coating, for example but not limited to, collagen, chitosan, gelatin, alginate or the like, onto the surface of the material to which cells can adhere or the surface of the material to which cells cannot adhere, thereby facilitating adhesion of the cells. Surface microstructurization is achieved by, for example, performing laser cutting on the surface of the material to which cells can adhere or the surface of the material to which cells cannot adhere so as to form microchannels, thereby facilitating adhesion of the cells. However, the processing methods of the disclosure are not limited thereto, and any processing method capable of enhancing cell adhesion properties may be applied in the disclosure.

A material of the reactor 110, the first fixer 120 and the second fixer 130A includes, for example, polyester (PET), nylon, polyethylene (PE), polypropylene (PP), polyvinyl chloride (PVC), polystyrene (PS), ethylene vinyl acetate (EVA), polyurethane (PU), polycarbonate (PC), glass or the like. However, the disclosure is not limited thereto.

In one exemplary embodiment, the inlet/outlet T12 of the cell culture carrier module 100A may be disposed on one end portion of the reactor 110. When only one single inlet/outlet T12 is disposed in the cell culture carrier module 100A, the inlet/outlet T12 may be used both for entry and exit of a liquid such as a culture medium and a buffer solution and for cell collection. However, in other exemplary embodiments, the entry and exit of the culture medium and the buffer solution and the cell collection may respectively use different channels, in view of preventing the whole module from contamination. In detail, the cell culture carrier module 100A of the present embodiment may include a plurality of inlets/outlets T12, T14, T16, T18 (not illustrated), T21 and T23, wherein the inlet/outlet T12 is disposed on one end portion of the reactor 110 and enables the cell collection. The inlets/outlets T14, T16 and T18 may be disposed on a side surface of the reactor 110 and close to the end portion of the reactor 110 on which the inlet/outlet T12 is disposed, so as to allow entry of different buffer solutions and culture media into the reactor 110. It should be noted that the numbers of the inlets/outlets T14, T16 and T18 may vary depending on the type and requirements of the actually injected liquid, and are not limited to those mentioned herein. The inlets/outlets T21 and T23 are disposed on the other end portion of the reactor 110, opposite the inlet/outlet T12. The inlet/outlet T21 allows the entry and exit of liquid such as a culture medium or a buffer solution, and the inlet/outlet T23 is a reserved hole, wherein the design in which the inlet/outlet T21 is located opposite the inlets/outlets T14, T16 and T18 facilitates distribution and circulation of liquid within the chamber C10.

The cell culture carrier module 100A of the present embodiment may further include a turbulent part 150 disposed in the chamber C10 and between the inlet/outlet T12 and the first fixer 120. To be specific, the turbulent part 150 may be arranged at the same plane height as the inlets/outlets T14, T16 and T18. The liquid that enters via the inlets/outlets T14, T16 and T18, after being rotated by the turbulent part 150, may drive circulation of the liquid in the chamber C10. As a result, substances in the liquid in the chamber C10 can be uniformly distributed, and the cells can be smoothly removed without accumulating at the bottom of the chamber C10 after completion of the culture.

The cell culture carrier module may have different designs depending on whether it is reusable. When the cell culture carrier module is reusable, as shown in the present embodiment, the reactor 110 of the cell culture carrier module 100A further includes a body 112 and a cover 114, the body 112 and the cover 114 being connected with each other to form the chamber C10. By opening the cover 114, the communication with the chamber C10 becomes possible so that the cell culture carriers 140 can be replaced. In addition, a sealing part 116 may further be disposed between the body 112 and the cover 114 to maintain sealability of the chamber C10. When the cell culture carrier module is for one time use only, the reactor 110 is integrally formed and a two-piece design is unnecessary.

FIG. 2A and FIG. 2B are schematic views of a cell culture carrier of a cell culture carrier module, in an untwisted state and a twisted state, respectively, according to another exemplary embodiment. Referring to FIG. 2A and FIG. 2B, a cell culture carrier module 100B of the present embodiment is similar to the cell culture carrier module 100A of FIG. 1A. Nonetheless, it should be noted that the cell culture carrier module 100B of the present embodiment further includes a magnetic control part 160A. Correspondingly, a second fixer 130B of the present embodiment has magnetism. Accordingly, the magnetic control part 160A may control the second fixer 130B to move, using magnetic force such as magnetic attractive force or magnetic repulsive force. As shown in FIG. 2A, when the magnetic control part 160A magnetically controls the second fixer 130B to move to a position away from the first fixer 120, the cell culture carriers 140 are rendered in the untwisted state. As shown in FIG. 2B, when the magnetic control part 160A controls the second fixer 130B to move to a position close to the first fixer 120, the cell culture carriers 140 are rendered in the twisted state. The shape of the magnetic control part 160A of the present embodiment roughly matches the shape of the reactor 110. Moreover, the magnetic control part 160A itself is movable, thereby driving the second fixer 130B to move. However, the disclosure is not limited thereto.

Figure 3:
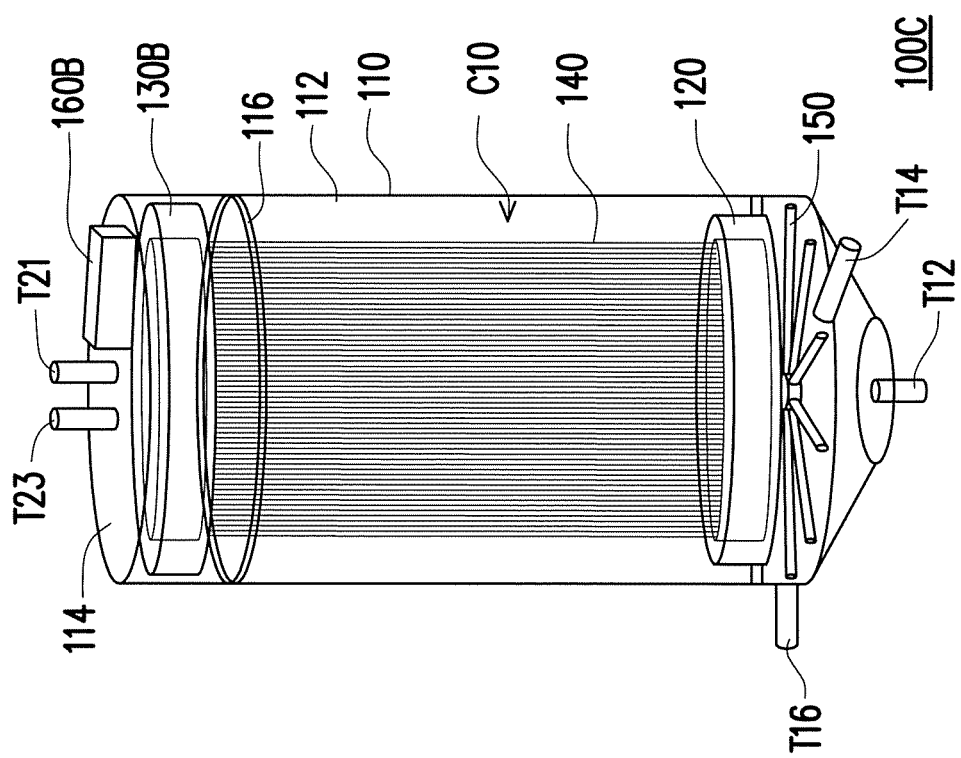
FIG. 3 is a schematic view of a cell culture carrier module according to still another exemplary embodiment.

FIG. 3 is a schematic view of a cell culture carrier module according to still another exemplary embodiment. Referring to FIG. 3, a cell culture carrier module 100C of the present embodiment is similar to the cell culture carrier module 100B of FIG. 2A. Nonetheless, it should be noted that, when a magnetic control part 160B of the present embodiment intends to control the second fixer 130B to move, the magnetic control part 160B directly moves to one side of the reactor 110 away from the first fixer 120 and then uses magnetic force to attract the second fixer 130B to move to a position away from the first fixer 120. By contrast, after the magnetic control part 160B is removed, the second fixer 130B will move to a position close to the first fixer 120 due to its own gravity.

FIG. 4A and FIG. 4B are schematic views of a cell culture carrier of a cell culture carrier module, in a twisted state and an untwisted state, respectively, according to yet still another exemplary embodiment. Referring to FIG. 4A and FIG. 4B, a cell culture carrier module 100D of the present embodiment is similar to the cell culture carrier module 100A of FIG. 1A. Nonetheless, it should be noted that the cell culture carrier module 100D of the present embodiment further includes a fastener 170. In addition, a reactor 110A further includes an elastic corrugated structure 110A1. When no force is applied thereto, the elastic corrugated structure 110A1 is, for example, in a stretched state as shown in FIG. 4B. The fastener 170 is configured to control the elastic corrugated structure 110A1 to remain in a compressed state or not, so that the elastic corrugated structure 110A1 can switch between the stretched state as shown in FIG. 4B and the compressed state as shown in FIG. 4A. A second fixer 130C of the present embodiment is fixed to the reactor 110A, and the elastic corrugated structure 110A1 is located between the first fixer 120 and the second fixer 130C. When the fastener 170 is fastened, the elastic corrugated structure 110A1 is in the compressed state. Thus, the first fixer 120 and the second fixer 130C approach each other to render the cell culture carriers 140 in the twisted state. When the fastener 170 is released, the elastic corrugated structure 110A1 is in the stretched state. Thus, the first fixer 120 and the second fixer 130C are away from each other to render the cell culture carriers 140 in the untwisted state.

Figure 5:
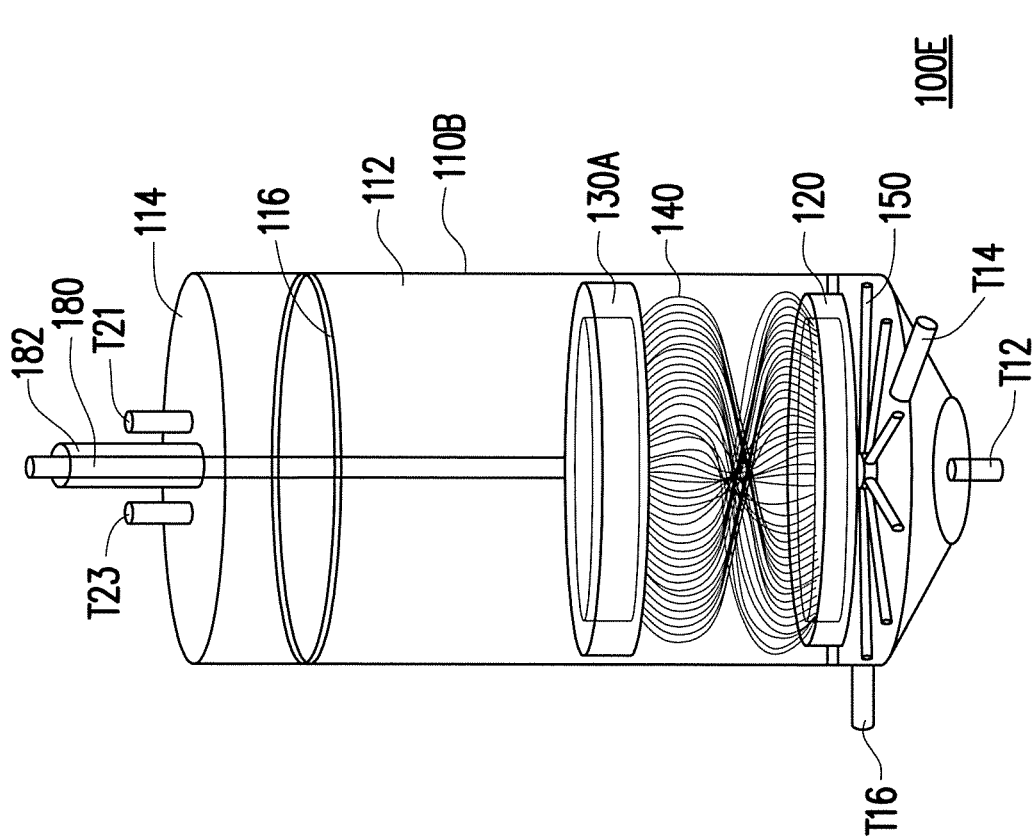
FIG. 5 is a schematic view of a cell culture carrier module according to further still another exemplary embodiment.

FIG. 5 is a schematic view of a cell culture carrier module according to further still another exemplary embodiment. Referring to FIG. 5, a cell culture carrier module 100E of the present embodiment is similar to the cell culture carrier module 100A of FIG. 1A. Nonetheless, it should be noted that the cell culture carrier module 100E of the present embodiment further includes a rod 180 and a guide hole 182. The guide hole 182 is disposed on one end of a reactor 110B, opposite the first fixer 120, so as to guide the rod 180 to be movably inserted through the reactor 110B. The rod 180 is connected to the second fixer 130A and configured to control the second fixer 130A to move. By controlling the extent to which the rod 180 is inserted into the reactor 110B, it is possible to control the second fixer 130A to move to a position close to or away from the first fixer 120.

Figure 6:
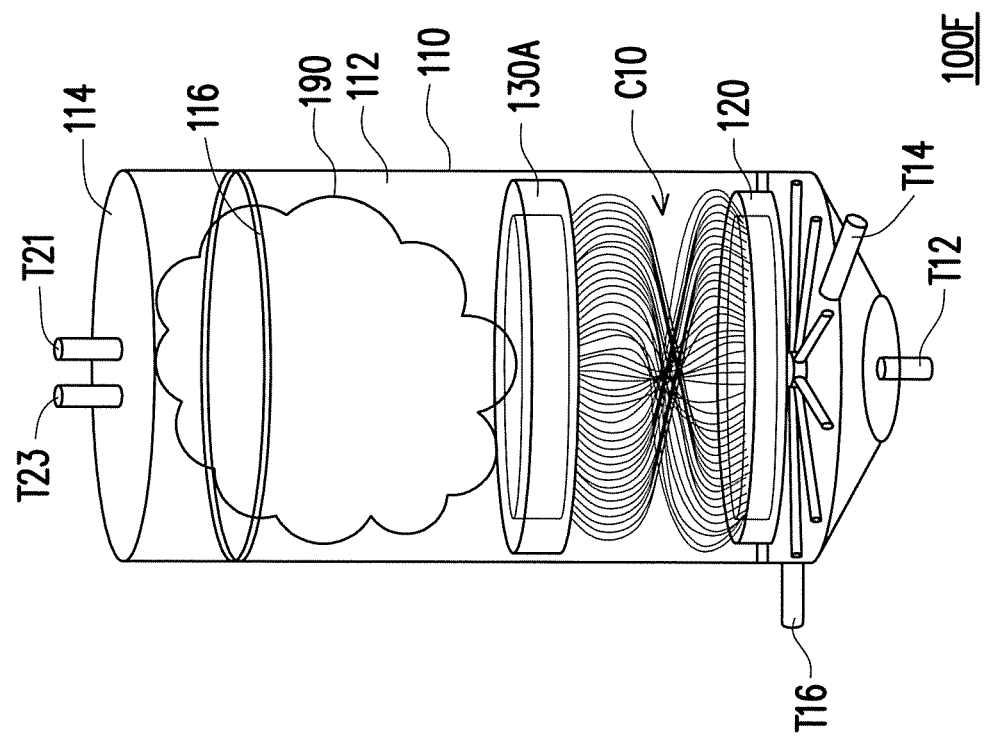
FIG. 6 is a schematic view of a cell culture carrier module according to another exemplary embodiment.

FIG. 6 is a schematic view of a cell culture carrier module according to another exemplary embodiment. Referring to FIG. 6, a cell culture carrier module 100F of the present embodiment is similar to the cell culture carrier module 100A of FIG. 1A. Nonetheless, it should be noted that the cell culture carrier module 100F of the present embodiment further includes a fluid pressure control part 190 disposed in the reactor 110 and inside the chamber C10. The second fixer 130A is located between the fluid pressure control part 190 and the first fixer 120. The fluid pressure control part 190 is configured to control the second fixer 130A to move. For example, the fluid pressure control part 190 is applicable to bags for containing fluids. However, the disclosure is not limited thereto. As a gas, water, oil or other fluid contained in the fluid pressure control part 190 increases, the volume of the fluid pressure control part 190 also increases, thus pushing the second fixer 130A to move in a direction approaching the first fixer 120. As the gas, water, oil or other fluid contained in the fluid pressure control part 190 decreases, the volume of the fluid pressure control part 190 also decreases, thus allowing the second fixer 130A to move in a direction away from the first fixer 120.

Figure 7:
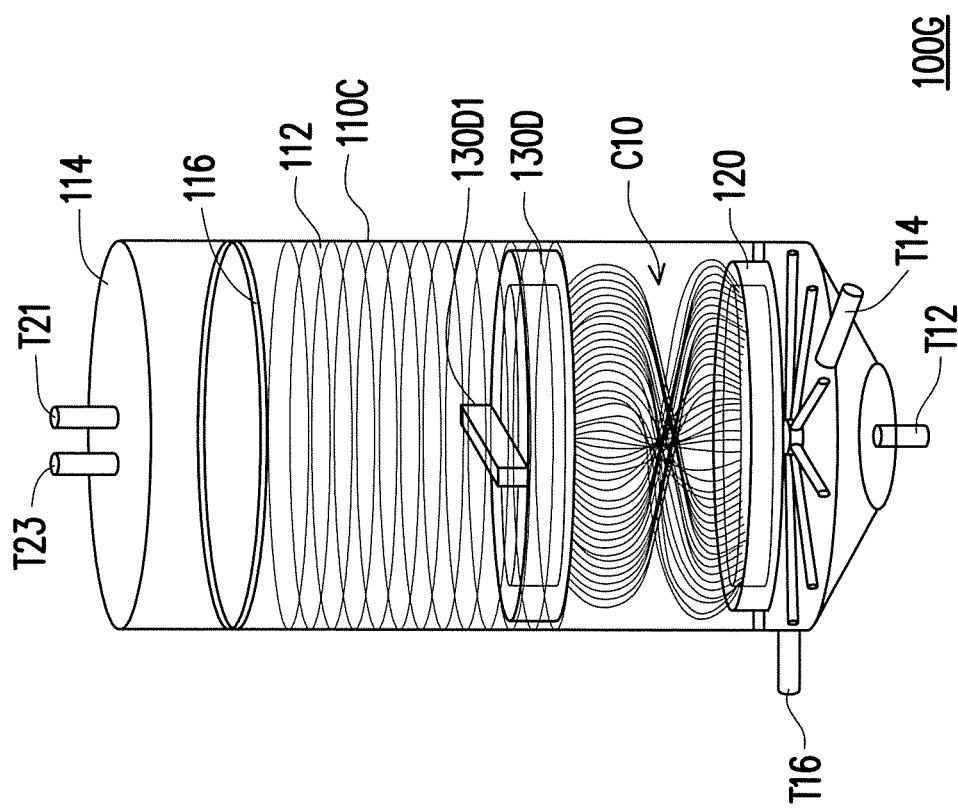
FIG. 7 is a schematic view of a cell culture carrier module according to still another exemplary embodiment.

FIG. 7 is a schematic view of a cell culture carrier module according to still another exemplary embodiment. Referring to FIG. 7, a cell culture carrier module 100G of the present embodiment is similar to the cell culture carrier module 100A of FIG. 1A. Nonetheless, it should be noted that, in the cell culture carrier module 100G of the present embodiment, a second fixer 130D is screwed onto a wall of a reactor 110C. In other words, screw threads matching each other are provided on contact surfaces of both the second fixer 130D and the reactor 110C. Accordingly, when the second fixer 130D is rotated relative to the reactor 110C, the second fixer 130D approaches or departs from the first fixer 120. A knob 130D1 is further provided on the second fixer 130D of the present embodiment to enable a user to easily apply force to rotate the second fixer 130D.

Figure 8A:
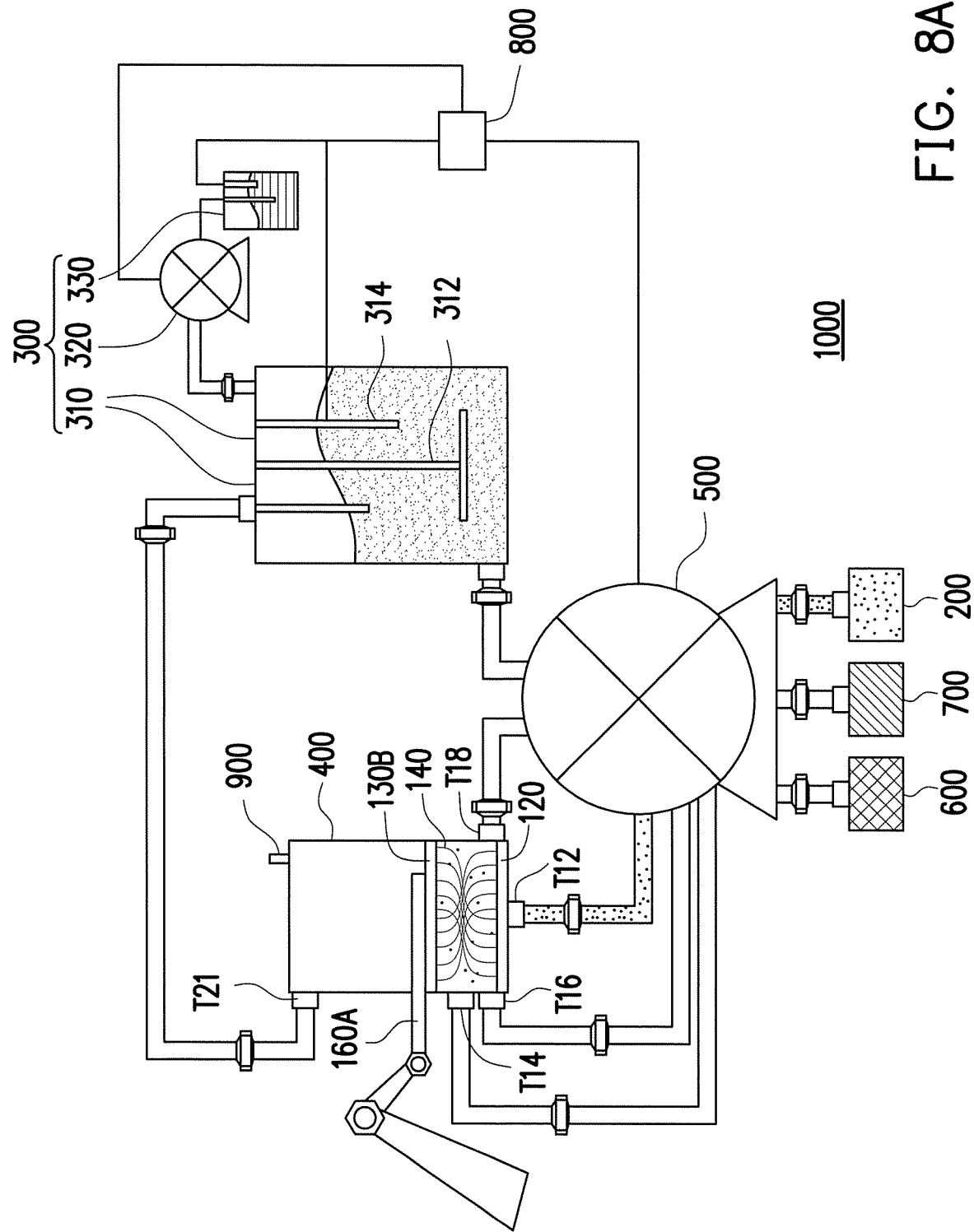
FIG. 8A to FIG. 8F are schematic views illustrating several stages of a cell culture performed by a cell culture system according to an exemplary embodiment.

FIG. 8A to FIG. 8F are schematic views illustrating several stages of a cell culture performed by a cell culture system according to an exemplary embodiment. Referring first to FIG. 8A, a cell culture system 1000 of the present embodiment includes a cell tank 200, a culture medium module 300 and a carrier module 400. The cell tank 200 and the culture medium module 300 respectively communicate with the carrier module 400. The carrier module 400 may be any cell culture carrier module of the aforesaid embodiments or any other cell culture carrier module complying with the spirit of the disclosure. The details of the carrier module 400 are omitted herein. Since the cell culture system 1000 of the present embodiment uses the carrier module 400 that is the same as the cell culture carrier module of the aforesaid embodiments, the cell culture system 1000 of the present embodiment can enhance the yield and the recovery rate of cell culture. In addition, the cell culture system 1000 of the present embodiment may optionally further include a pump 500, a cleaning solution tank 600 and a cell detachment enzyme tank 700. The cell tank 200 and the culture medium module 300 respectively communicate with the carrier module 400 via the pump 500. Both the cleaning solution tank 600 and the cell detachment enzyme tank 700 also communicate with the carrier module 400 via, for example, the pump 500.

In the present embodiment, the cell tank 200, the culture medium module 300, the cleaning solution tank 600 and the cell detachment enzyme tank 700 all communicate with the carrier module 400 via the pump 500. The cell tank 200 is connected to the pump 500 by which the cell tank 200 is connected to the inlet/outlet T12 of the carrier module 400. The cleaning solution tank 600 is connected to the pump 500 by which the cleaning solution tank 600 is connected to the inlet/outlet T14 of the carrier module 400. The cell detachment enzyme tank 700 is connected to the pump 500 by which the cell detachment enzyme tank 700 is connected to the inlet/outlet T16 of the carrier module 400. The culture medium module 300 is connected to the pump 500 by which the culture medium module 300 is connected to the inlet/outlet T18 of the carrier module 400. The culture medium of the culture medium module 300 enters the carrier module 400 via the inlet/outlet T18, and then flows back from the carrier module 400 to the culture medium module 300 via the inlet/outlet T21 on the other end. Therefore, the culture medium of the culture medium module 300 can be recycled for use. To monitor quality of the culture medium of the culture medium module 300, a culture medium tank 310 of the culture medium module 300 is equipped with a culture medium sensor 314. The culture medium sensor 314 is, for example, a pH meter, a thermometer, or a dissolved oxygen meter. In addition, a stirring bar 312 is further disposed in the culture medium tank 310 to maintain uniform distribution of culture substances in the culture medium. In addition, the culture medium module 300 is further equipped with a pump 320 and a regulator 330. When the culture medium sensor 314 senses that the quality of the culture medium in the culture medium tank 310 is lower than a threshold value, the pump 320 extracts regulating substances from the regulator 330 into the culture medium tank 310 so as to improve the quality of the culture medium. The cell culture system 1000 of the present embodiment may further include a controller 800 configured to control the pump 500, the pump 320, the regulator 330 and the culture medium sensor 314. In addition, the cell culture system 1000 of the present embodiment may further include a regulator 900 installed onto the carrier module 400, for regulating the substances in the carrier module 400 when necessary.

Figure 9:
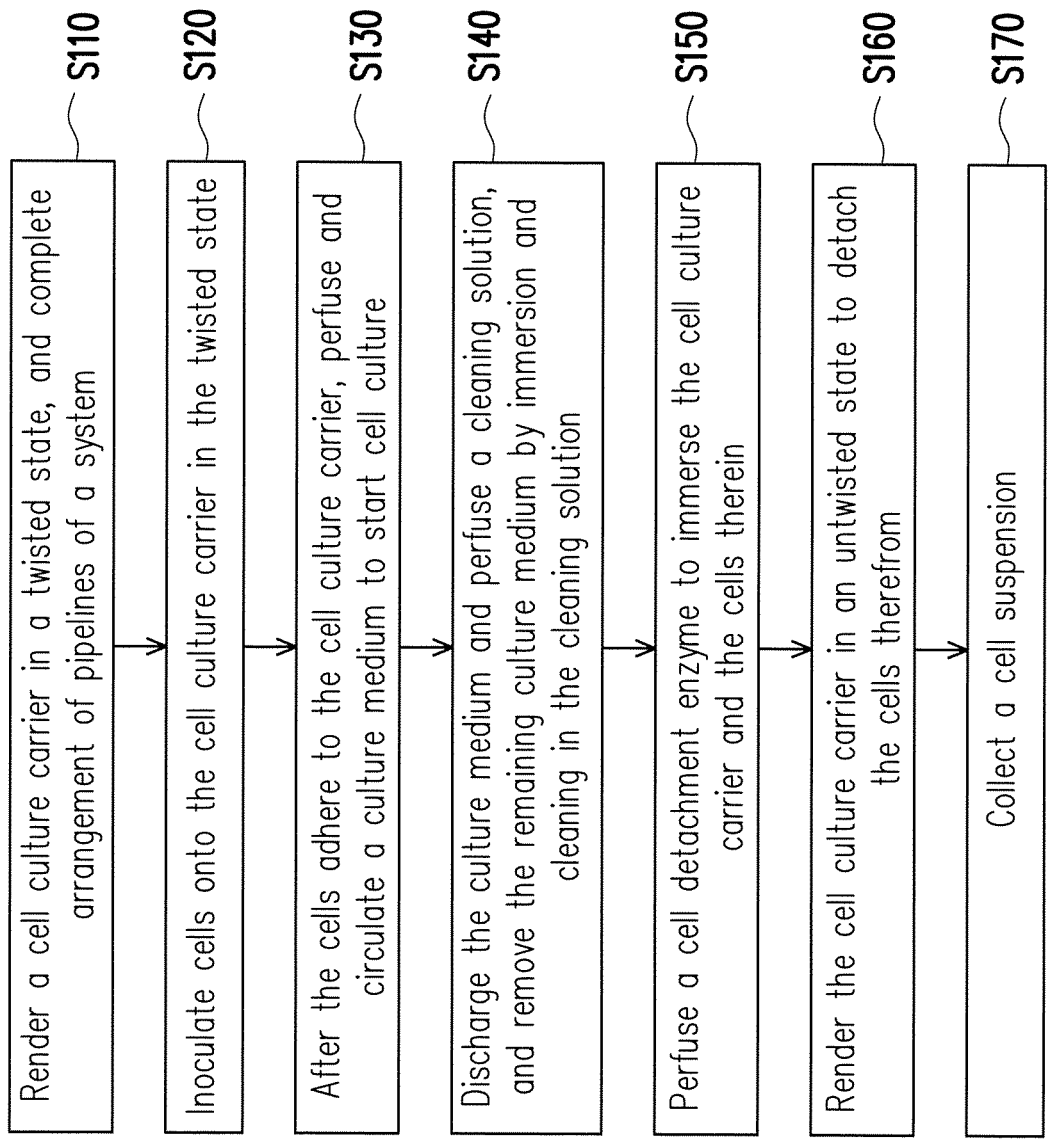
FIG. 9 is a flowchart of a cell culture method that may be performed by a cell culture system and a cell culture carrier module according to an exemplary embodiment.

FIG. 9 is a flowchart of a cell culture method that may be performed by a cell culture system and a cell culture carrier module according to an exemplary embodiment. Referring to FIG. 8A and FIG. 9, during a cell culture process, first of all, the cell culture carrier 140 of the carrier module 400 is rendered in a twisted state, and arrangement of pipelines of the system is completed (step S110). As mentioned in the aforesaid embodiments, a method of rendering the cell culture carrier 140 of the carrier module 400 in the twisted state includes causing the second fixer 130A to move to a position close to the first fixer 120. However, the way of performing the method is not limited. As in the aforesaid embodiments, the second fixer 130A may be displaced through gravity, magnetic force, or other mechanical force. In the present embodiment, the movement of the second fixer 130A may be controlled with the assistance of the magnetic control part 160A.

Referring to FIG. 8A and FIG. 9, next, cells in the cell tank 200 which are to be cultured are sent to the carrier module 400 using the pump 500, so as to inoculate the cells to be cultured onto the cell culture carrier 140 in the twisted state (step S120). The cells to be cultured are, for example but not limited to, stem cells or differentiated cells. Specifically, the cells to be cultured are, for example but not limited to, African green monkey kidney cell line (Vero), human adipose-derived stem cells (ADSCs), mesenchymal stem cells (MSCs), Madin-Darby Canine Kidney (MDCK) cells, human embryonic kidney cells 293 (HEK 293 cells) or the like. In the present embodiment, a culture medium is first added to the cell culture carrier 140, and the cells are then inoculated to the cell culture carrier 140. In another exemplary embodiment, a cell culture medium containing the cells may be uniformly added directly to the cell culture carrier 140. The culture medium is a standard growth culture medium commonly used for cell culture, and examples thereof include a culture medium having fetal bovine serum (FBS) or a serum-free medium. However, the disclosure is not limited thereto. In addition, it should be understood that, depending on different cell properties, requirements of operating concentration of the cell culture medium is different. Hence, the operating concentration may be adjusted according to cell properties, and growth factors, antibiotics or the like may be added to the culture medium if needed. The cells are caused to adhere to the cell culture carrier. In the present embodiment, the cell culture carrier 140 is placed in the carrier module 400 under specific growth conditions (e.g., specific temperature, humidity, or carbon dioxide concentration) such that the cells adhere to the cell culture carrier 140.

Figure 8B:
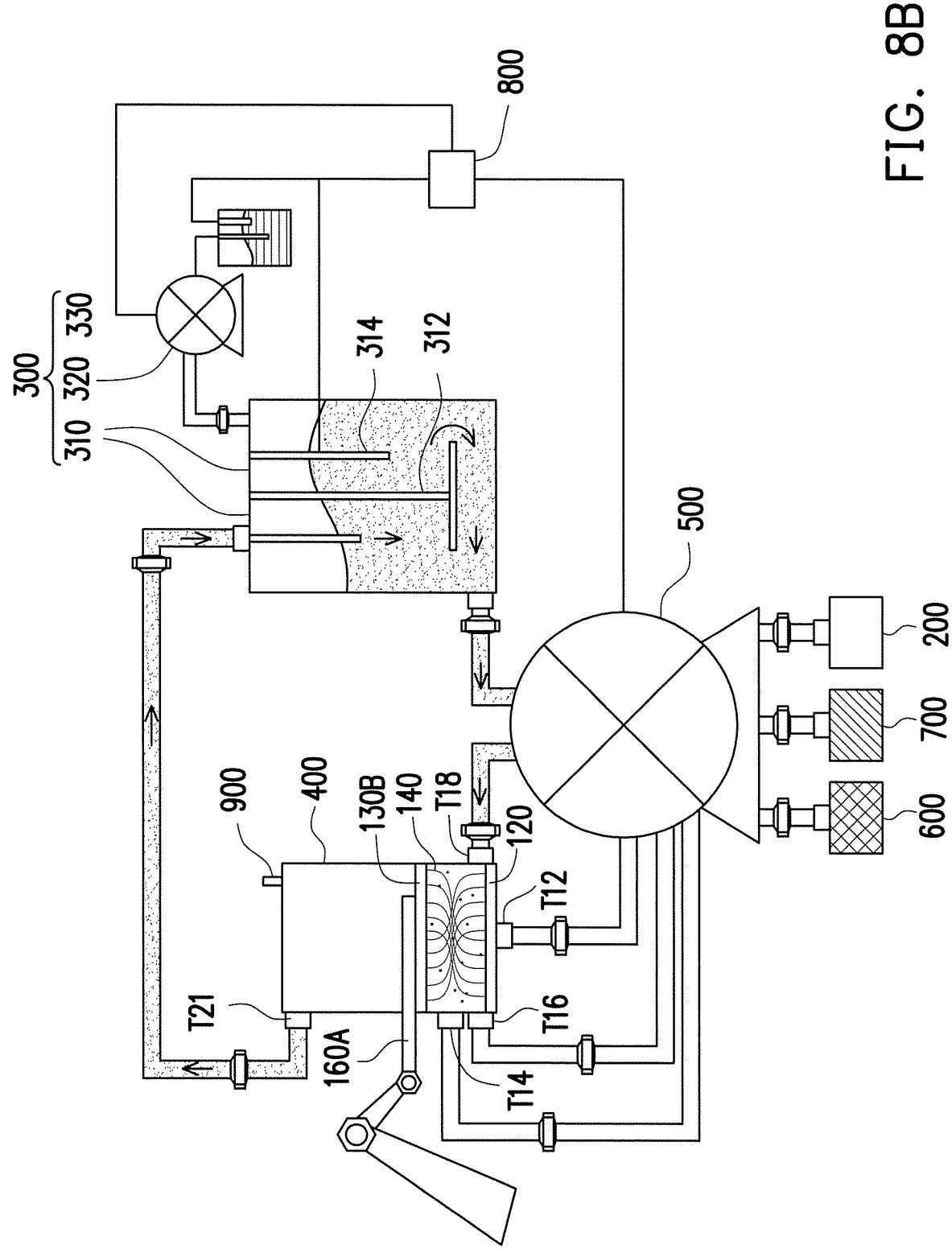

Referring to FIG. 8B and FIG. 9, next, after the cell adhesion, a culture medium is perfused and circulated to start the cell culture (step S130). That is, after the aforesaid steps are completed, the pump 500 may be turned on to allow the culture medium of the culture medium module 300 to flow into the carrier module 400, and the culture medium is continuously circulated between the culture medium module 300 and the carrier module 400 so as to culture the cells. The cell culture is performed by, for example, static culture or dynamic culture. The dynamic culture may be performed by disturbing the culture medium surrounding the cell culture carrier. A method of disturbing the culture medium includes, for example, using the turbulent part 150 as in FIG. 1A, which is but not illustrated in the present embodiment. In one exemplary embodiment, the number of cells after culture may increase to 100 times or more the original number of cells. In another exemplary embodiment, the number of cells after culture may increase to 2000 times or more the original number of cells.

It is noting that since different cells have different properties, the cell culture conditions may be adjusted based on different cell types. For example, when culturing mammalian cells, the cells may be cultured at conditions of 37° C. and 5% of $CO_2$, and the pH value of the culture medium is maintained within a physiological range thereof. For example, for most animal cells, a suitable pH value of the culture medium is 7.2 to 7.4.

Figure 8C:
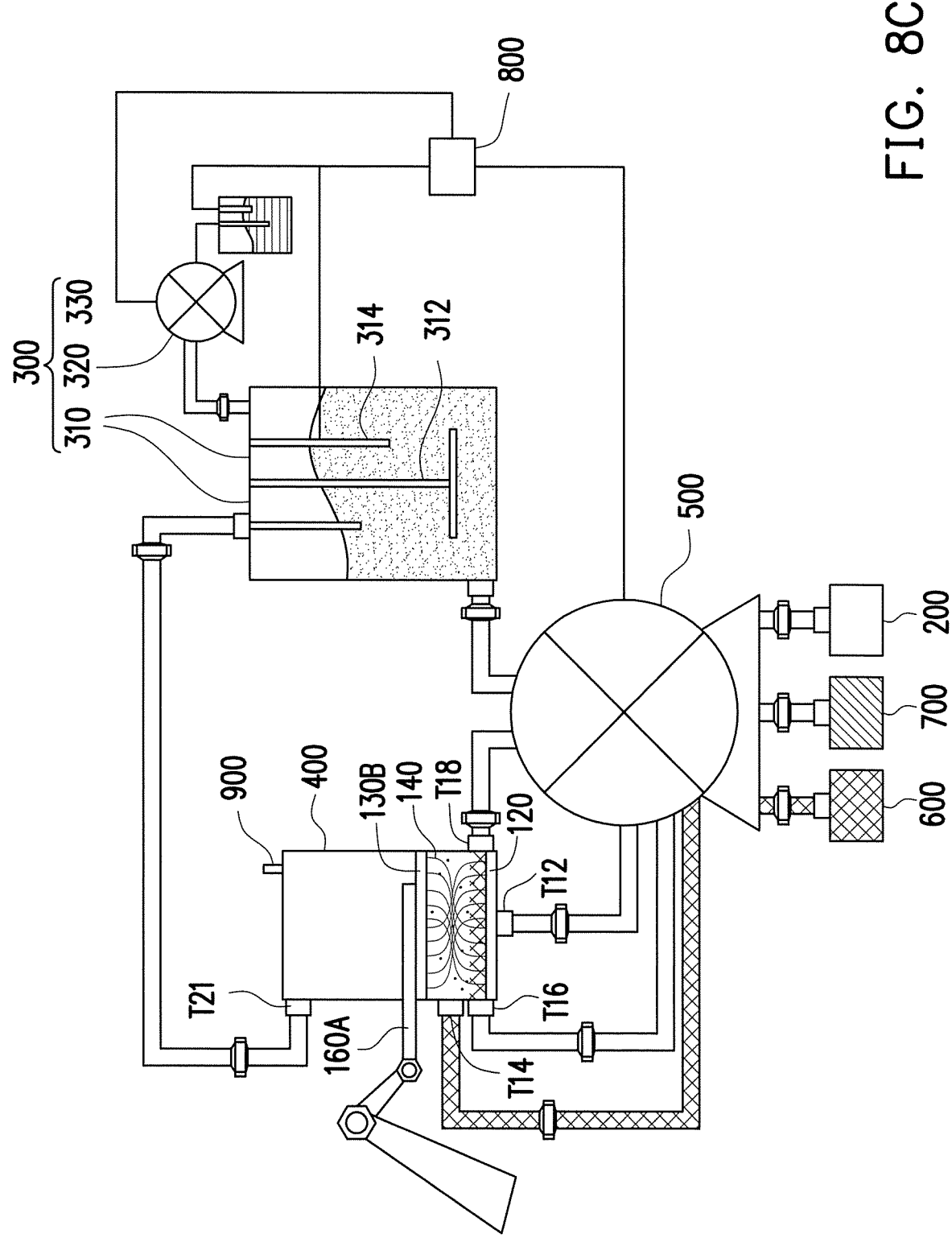

Referring to FIG. 8C and FIG. 9, next, the culture medium is discharged and a cleaning solution is perfused, and the remaining culture medium is removed by immersion and cleaning in the cleaning solution (step S140). That is, all of the culture medium in the carrier module 400 is sent back to the culture medium module 300. Then, the cleaning solution in the cleaning solution tank 600 is caused to flow into the carrier module 400 by the pump 500, and the remaining culture medium is removed by immersion and cleaning in the cleaning solution. The cleaning solution is, for example, a phosphate buffered saline solution.

Figure 8D:
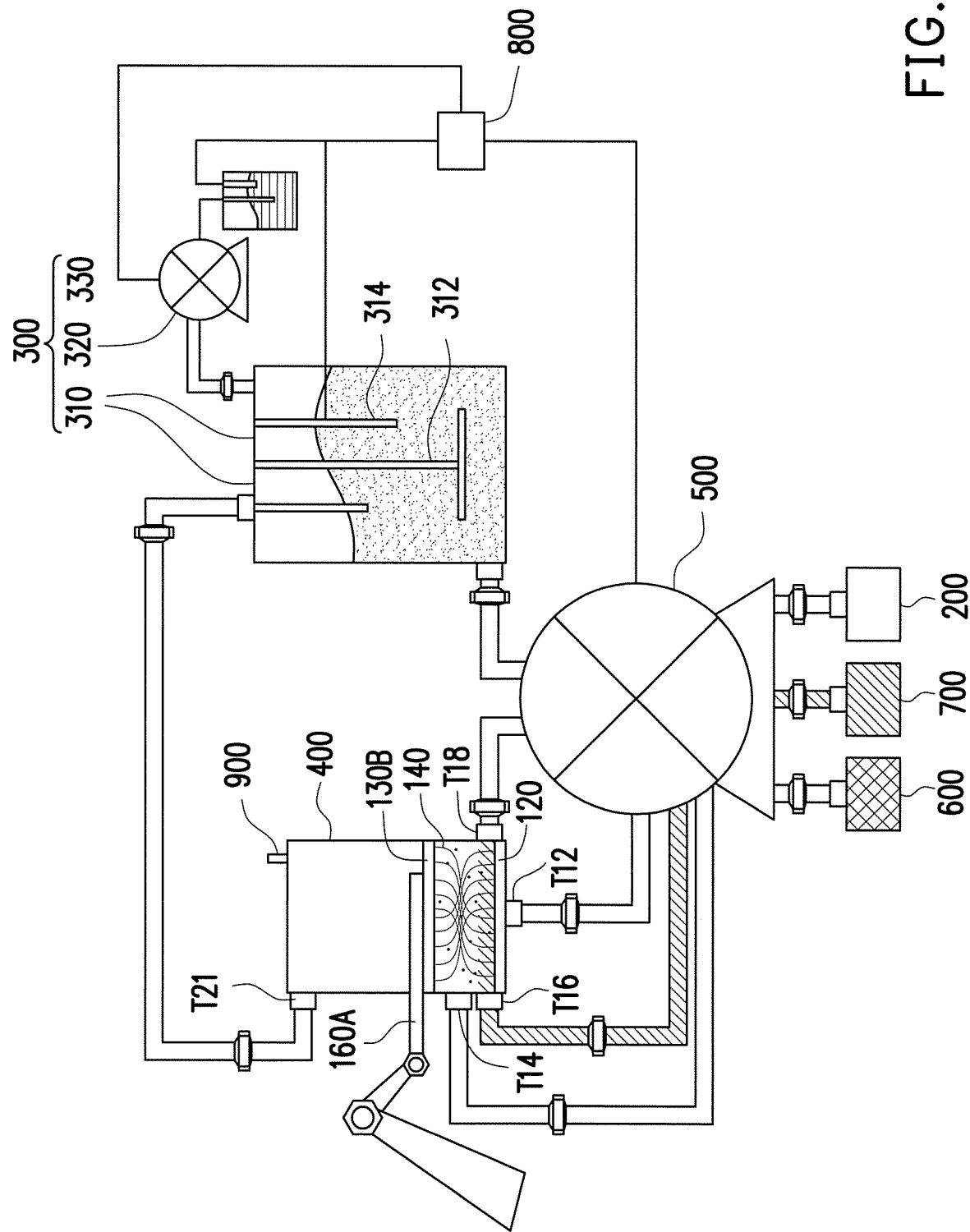

Referring to FIG. 8D and FIG. 9, next, a cell detachment enzyme is perfused to immerse the cell culture carrier and the cells therein (step S150). That is, all of the cleaning solution in the carrier module 400 is sent back to the cleaning solution tank 600. Then, the cell detachment enzyme in the cell detachment enzyme tank 700 is caused to flow into the carrier module 400 by the pump 500, and the cell culture carrier 140 in the twisted state and the cells are immersed in the cell detachment enzyme. The cell detachment enzyme is, for example, trypsin, tryp LE, accutase, accumax, or collagenase. However, the disclosure is not limited thereto, and other enzyme or reagent capable of cell detachment may also be used.

Figure 8E:
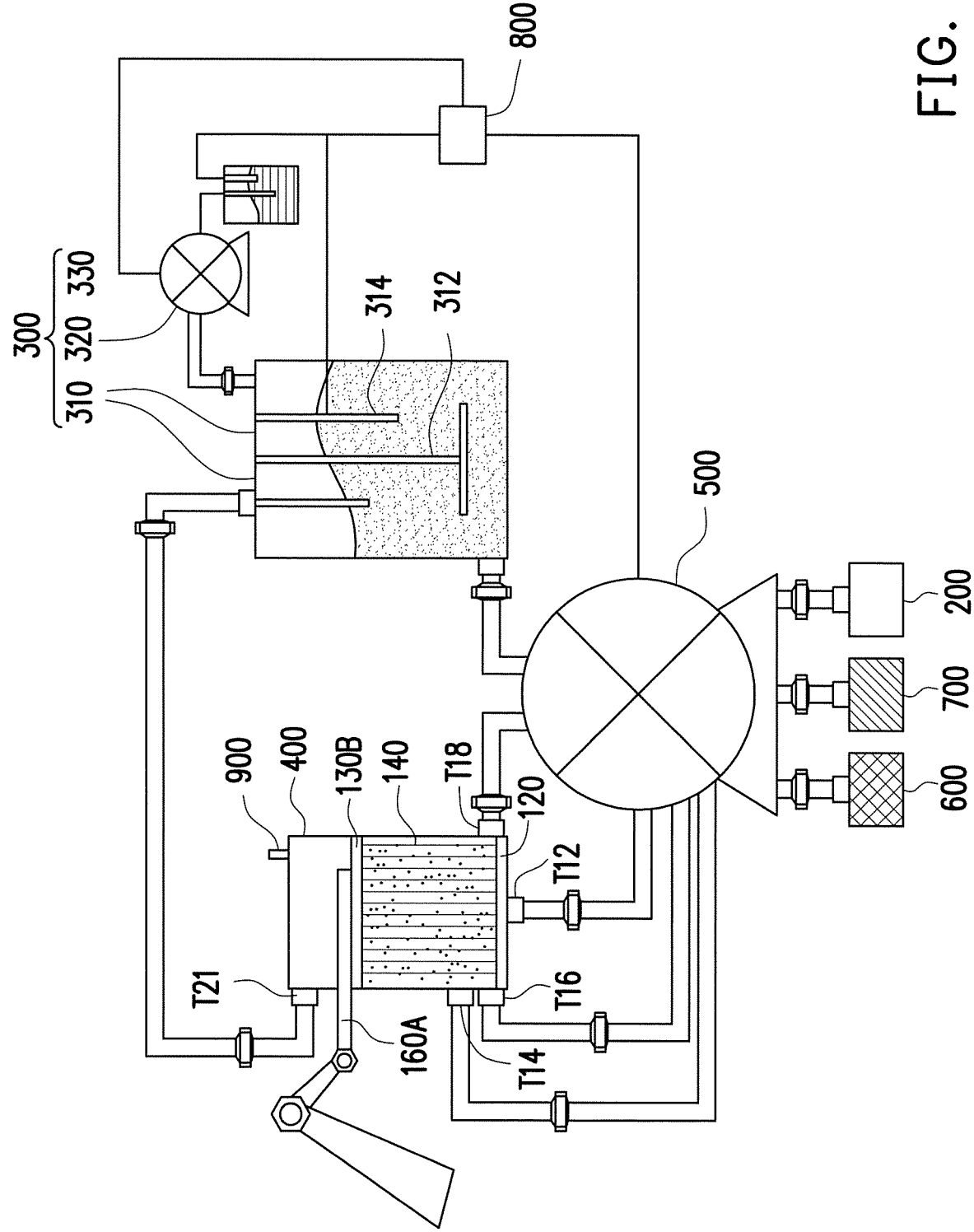

Referring to FIG. 8E and FIG. 9, next, the cell culture carrier is loosened and transformed into a two-dimensional structure, causing detachment of the cells (step S160). That is, the cell culture carrier 140 of the carrier module 400 is changed from the twisted state to an untwisted state. As mentioned in the aforesaid embodiments, a method of rendering the cell culture carrier 140 of the carrier module 400 in the untwisted state includes causing the second fixer 130A to move to a position away from the first fixer 120. In the present embodiment, the movement may be performed with the assistance of the magnetic control part 160A.

Figure 8F:
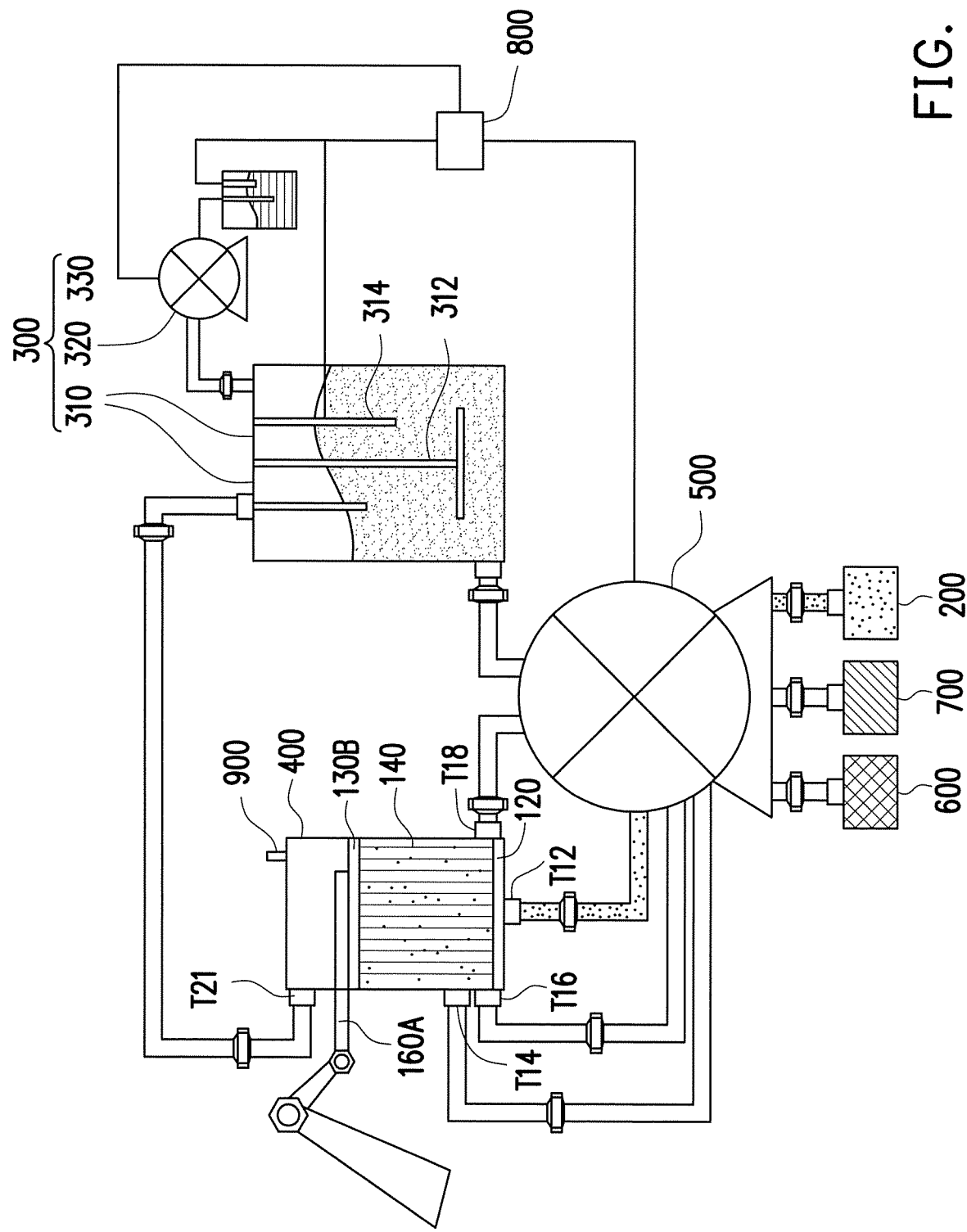

Referring to FIG. 8F and FIG. 9, next, a cell suspension is collected (step S170). That is, a cell suspension in the carrier module 400 is sent to the cell tank 200 through the pump 500. Since the cell recovery is performed when the cell culture carrier 140 is in the untwisted state, the loosened structure allows the cell culture carrier 140 to sufficiently react with a reagent containing the cell detachment enzyme, and the loosened structure also facilitates the detachment of the cells on an inner layer of the cell culture carrier 140, thereby enhancing the cell recovery rate.

It should be noted that, in the aforesaid embodiments, the cell culture carrier 140 is loosened after the cell detachment enzyme is perfused, and the cells are then collected. However, in other exemplary embodiments, the cell culture carrier 140 may first be loosened to return to the two-dimensional state. The cell detachment enzyme is then perfused to collect the cultured cells. The disclosure is not limited to the above description.

In summary, in the cell culture carrier module and the cell culture system according to one or more exemplary embodiments, since the second fixer is movable, the cell culture carrier may switch between the untwisted state and the twisted state as the distance between the first fixer and the second fixer on two ends of the cell culture carrier varies. The cell culture carrier in the twisted state conduces to enhancement of the quality and yield of cell culture; the cell culture carrier in the untwisted state conduces to enhancement of the cell recovery rate.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A cell culture carrier module, comprising:
   a reactor having a chamber and at least one inlet/outlet, wherein the at least one inlet/outlet communicates with the chamber;
   a first fixer fixed to the reactor and located in the chamber;
   a second fixer disposed in the chamber and being movable relative to the first fixer; and
   a plurality of cell culture carriers, two ends of each of the cell culture carriers being fixed to the first fixer and the second fixer, respectively, wherein according to a variation in a distance between the first fixer and the second fixer due to a movement of the second fixer, the cell culture carriers are in an untwisted state or in a twisted state.

2. The cell culture carrier module according to claim 1, further comprising a magnetic control part, wherein the second fixer has magnetism, and the magnetic control part is configured to magnetically control the second fixer to move.

3. The cell culture carrier module according to claim 1, further comprising a fastener, wherein the reactor further comprises an elastic corrugated structure, the fastener is configured to control the elastic corrugated structure to switch between a stretched state and a compressed state, the second fixer is fixed to the reactor, and the elastic corrugated structure is located between the first fixer and the second fixer,
   when the elastic corrugated structure is in the stretched state, the cell culture carriers are in the untwisted state, and
   when the elastic corrugated structure is in the compressed state, the cell culture carriers are in the twisted state.

4. The cell culture carrier module according to claim 1, further comprising a rod movably inserted through the reactor and connected to the second fixer, the rod being configured to control the second fixer to move.

5. The cell culture carrier module according to claim 1, further comprising a fluid pressure control part disposed in the reactor and inside the chamber, wherein the second fixer is located between the fluid pressure control part and the first fixer, and the fluid pressure control part is configured to control the second fixer to move.

6. The cell culture carrier module according to claim 1, wherein the second fixer is screwed onto a wall of the reactor.

7. The cell culture carrier module according to claim 1, further comprising a turbulent part disposed in the chamber and located between the at least one inlet/outlet and the first fixer.

8. The cell culture carrier module according to claim 7, wherein number of the at least one inlet/outlet is plural, and the plurality of inlets/outlets are respectively arranged on an end portion and a side surface of the reactor, and the at least one inlet/outlet located on the side surface is arranged at the same plane height as the turbulent part.

9. A cell culture system, comprising
a cell tank;
a culture medium module;
a carrier module, wherein the cell tank and the culture medium module respectively communicate with the carrier module, and the carrier module comprises:
  a reactor having a chamber and at least one inlet/outlet, wherein the at least one inlet/outlet communicates with the chamber;
  a first fixer fixed to the reactor and located in the chamber;
  a second fixer disposed in the chamber and being movable relative to the first fixer; and
  a plurality of cell culture carriers, two ends of each of the cell culture carriers being fixed to the first fixer and the second fixer, respectively, wherein according to a variation in a distance between the first fixer and the second fixer due to a movement of the second fixer, the cell culture carriers are in an untwisted state or in a twisted state.

10. The cell culture system according to claim 9, wherein the carrier module further comprises a magnetic control part, the second fixer has magnetism, and the magnetic control part is configured to magnetically control the second fixer to move.

11. The cell culture system according to claim 9, wherein the carrier module further comprises a fastener, the reactor further comprises an elastic corrugated structure, the fastener is configured to control the elastic corrugated structure to switch between a stretched state and a compressed state, the second fixer is fixed to the reactor, and the elastic corrugated structure is located between the first fixer and the second fixer,
wherein when the elastic corrugated structure is in the stretched state, the cell culture carriers are in the untwisted state, and
when the elastic corrugated structure is in the compressed state, the cell culture carriers are in the twisted state.

12. The cell culture system according to claim 9, wherein the carrier module further comprises a rod movably inserted through the reactor and connected to the second fixer, and the rod is configured to control the second fixer to move.

13. The cell culture system according to claim 9, wherein the carrier module further comprises a fluid pressure control part disposed in the reactor and inside the chamber, wherein the second fixer is located between the fluid pressure control part and the first fixer, and the fluid pressure control part is configured to control the second fixer to move.

14. The cell culture system according to claim 9, wherein the second fixer is screwed onto a wall of the reactor.

15. The cell culture system according to claim 9, further comprising a turbulent part disposed in the chamber and located between the at least one inlet/outlet and the first fixer.

16. The cell culture system according to claim 15, wherein number of the at least one inlet/outlet is plural, and the plurality of inlets/outlets are respectively arranged on an end portion and a side surface of the reactor, and the at least one inlet/outlet located on the side surface is arranged at the same plane height as the turbulent part.

17. The cell culture system according to claim 9, further comprising a pump, wherein the cell tank and the culture medium module respectively communicate with the carrier module via the pump.

18. The cell culture system according to claim 9, further comprising a cleaning solution tank communicating with the carrier module.

19. The cell culture system according to claim 9, further comprising a cell detachment enzyme tank communicating with the carrier module.

* * * * *